(12) United States Patent
Lin et al.

(10) Patent No.: US 8,409,262 B2
(45) Date of Patent: *Apr. 2, 2013

(54) COMPOSITION USED FOR INCREASING CALMODULIN AND METHOD THEREOF

(75) Inventors: Yung-Sheng Lin, Changhua County (TW); Ting-Kai Leung, Taipei (TW); Jiann-Shiun Kao, Taipei (TW)

(73) Assignee: National Applied Research Laboratories, Taipei (TW)

( * ) Notice: Subject to any disclaimer, the term of this patent is extended or adjusted under 35 U.S.C. 154(b) by 836 days.

This patent is subject to a terminal disclaimer.

(21) Appl. No.: 12/562,937

(22) Filed: Sep. 18, 2009

(65) Prior Publication Data

US 2011/0046701 A1   Feb. 24, 2011

(30) Foreign Application Priority Data

Aug. 24, 2009   (TW) ................................ 98128436 A (51) Int. Cl.
*A61N 5/06* (2006.01)
(52) U.S. Cl. ........................................................ 607/88
(58) Field of Classification Search .................. 607/88, 607/91, 96, 99
See application file for complete search history.

(56) References Cited

U.S. PATENT DOCUMENTS

| 6,989,368 B2 | 1/2006 | McMichael | |
|---|---|---|---|
| 2004/0266601 A1* | 12/2004 | Tsai | 501/19 |
| 2008/0311059 A1* | 12/2008 | Lin et al. | 424/59 |

FOREIGN PATENT DOCUMENTS

| TW | 482747 B | 12/1986 |
| TW | 593204 B | 8/1992 |
| TW | M362649 U1 | 8/2009 |

OTHER PUBLICATIONS

Shiurba et al, Cellular responses of the ciliate, *Tetrahymena thermophila*, to far infrared irradiation, Aug. 4, 2006, Royal Society of Chemistry and Owner Societies, Photochemical and Photobiological Sciences, 2006, 5, 799-807.*
English abstracts of TW 593204B, TW M362649U1, and TW 482747B.

* cited by examiner

*Primary Examiner* — James Greece
(74) *Attorney, Agent, or Firm* — WPAT, P.C.; Anthony King (57) ABSTRACT

The present invention provides a composition used for increasing calmodulin and a method thereof. A far-infrared ray is released by a far-infrared releasing substance in the composition so as to induce intracellular calmodulin concentration increased in organisms. The far-infrared releasing substance consists of ceramic minerals and mainly comprises 80-99.9 wt % of oxide minerals including 60-95 wt % of the mineral alumina. The far-infrared releasing substance according to the present invention has the advantages of easy to carry and continuously working, so as to significantly improve the shortcoming of drugs with short-term acting.

9 Claims, 8 Drawing Sheets

COMPOSITION USED FOR INCREASING CALMODULIN AND METHOD THEREOF

BACKGROUND OF THE INVENTION (a) Field of the Invention

The present invention relates to a composition used for increasing calmodulin and a method thereof, and more particularly to a composition which can irradiate an far-infrared ray with a specific wavelength to induce the expression of calmodulin and a method thereof.

(b) Description of the Prior Art

A far-infrared ray (FIR) is a short electromagnetic wave having a wavelength within the infrared spectrum. Among them, the far-infrared ray having a wavelength between 3-14 µm has been named the light of life as it helps in the growth of animals and plants. Currently, it has been proved medically that FIR has a therapeutic effect on many human diseases, and thus is often applied to many physiological purposes, for example, blood circulation acceleration, metabolism activation, tissue regeneration and immune system activation. The effects of far-infrared rays can be classified into the thermal effect and the non-thermal effect. The thermal effect comprises local tissue temperature increase, capillary expansion, blood flow rate increase, etc. The non-thermal effect comprises the influence on intracellular functions, such as stimulating cell proliferation to promote wound healing and enhancing the functions of immune cells.

In most current known techniques, a far-infrared source irradiates far-infrared rays using electric power. However, an external heat source is required in use, and it is not easy to carry. More seriously, some ingredients in far-infrared releasing substances contain excess rare elements. It is difficult to avoid doubt about radioactive radiation in use of their applied products.

Calmodulin is an important modulation factor in animal bodies, and has multiple biological functions, such as the functions of information transmission or intracellular material transport, modulation of intracellular calcium ion concentration, enzyme and hormone activation, nervous system modulation, metabolism enhancement, activation of macrophages, T cells among immune cells and enhancement of antimicrobial activity of leukocytes. U.S. Pat. No. 6,989,368 proposes calmodulin can be used for promoting bone regeneration to prevent osteoporosis. However, oral chemicals are currently used in modulation of calmodulin concentration and easy to cause a side effect. Furthermore, the function and activity of calmodulin in the brain declines with aging. Some normal intracellular functions are limited by the presence of calmodulin, so calmodulin present in cells is finite. However, many enzymes require calmodulin, so calmodulin cannot meet the needs of cells.

SUMMARY OF THE INVENTION

In view of the above-mentioned problems of the prior art, an object of the present invention is to provide a composition used for increasing calmodulin and a method thereof, so as to enhance production of calmodulin in a physical mechanism and avoid the side effect of oral drugs.

According to the object of the present invention, a composition used for increasing calmodulin is provided, comprising a far-infrared releasing substance. The far-infrared releasing substance consists of ceramic minerals and mainly comprises 80-99.9 wt % of an oxide mineral. Far-infrared rays released by the far-infrared releasing substance can enhance intracellular production of calmodulin.

Furthermore, the present invention provides a method for increasing calmodulin, comprising the steps of: providing a far-infrared releasing substance, and placing the far-infrared ray releasing substance in an appropriate distance from a subject so that a far-infrared ray released by the far-infrared releasing substance enhances intracellular calmodulin production in the subject. The far-infrared releasing substance may be a ceramic mineral and comprises 80-99.9 wt % of an oxide mineral. Besides, the appropriate distance of the far-infrared releasing substance from the subject is within an irradiation range of the far-infrared ray.

Moreover, the present invention provides a use of a far-infrared releasing substance. The far-infrared releasing substance can be used for enhancing intracellular production of calmodulin. It is a ceramic mineral and comprises 80-99.9 wt % of an oxide mineral.

As described above, the composition used for increasing calmodulin and the method thereof according to the present invention may have the following advantages:

(1) The composition used for increasing calmodulin and the method thereof according to the present invention uses the far-infrared ray as a emissive substance and thus can improve the diseases caused by deficiency of calmodulin in a simple physical mechanism, thereby reducing the dependence on oral drugs and their side effect.

(2) With no need of heating, the far-infrared releasing substance according to the present invention has high far-infrared emissivity at room temperature so that the composition comprising the far-infrared releasing substance has the advantages of easy to carry and continuously working, and thus improves the shortcoming of drugs with short-term acting.

(3) Although the composition provided by the present invention is a radioactive substance, it will not release ionization radiation and further contains negative ions good for the human body. Therefore, it can further ensure that the composition is safe and healthy for the user to use it.

BRIEF DESCRIPTION OF THE DRAWINGS

FIG. 3 shows the influence of the release time of far-infrared rays on the calmodulin contents in RAW 264.7 cells incubated without addition of LPS according to the present invention, wherein

FIG. 4 shows the influence of addition or no addition of LPS in incubation of RAW 264.7 cells on the calmodulin contents according to the present invention, wherein

DETAILED DESCRIPTION OF THE PREFERRED EMBODIMENTS

The present invention will be further described in detail with reference to the following preferred embodiments and the accompanying drawings.

EXAMPLE I

Composition for Increasing Calmodulin

The composition used for increasing calmodulin according to the present invention comprises a far-infrared releasing substance. Far-infrared rays released by the far-infrared releasing substance can enhance intracellular production of calmodulin. The far-infrared releasing substance may be a ceramic mineral and comprises 80-99.9 wt % of an oxide mineral, and the balance (0.1-20 wt %) may comprise such as titanium boride, zinc hydroxide or carbide. Besides, the oxide mineral mainly comprises 60-95 wt % of 1 alumina, and further comprises titanium dioxide, titanium boride, magnesium oxide, silicon oxide, ferric oxide or zinc oxide. In a preferred embodiment of the present invention, the far-infrared releasing substance consists of 60-95 wt % of alumina, 1-20 wt % of ferric oxide, 1-10 wt % of magnesium oxide, 1-10 wt % of zinc oxide, and 0.1-20 wt % of calcium carbonate.

Figure 1:
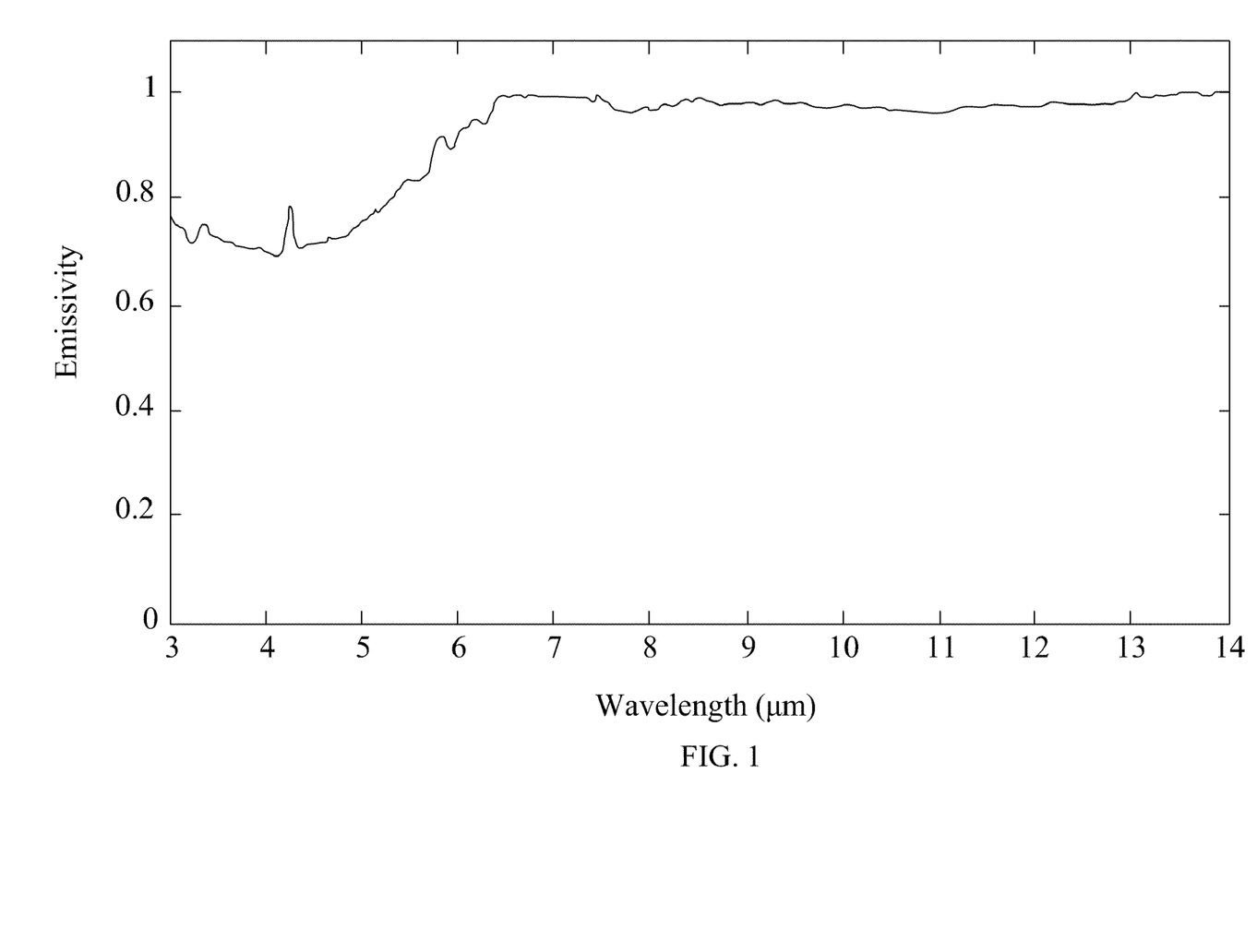
FIG. 1 is a curve diagram of the far-infrared emissivity of the far-infrared releasing substance according to the present invention.

Furthermore, the far-infrared releasing substance can irradiate a far-infrared ray at room temperature, which is measured by an FIR spectrometer using a black body as a standard to obtain the emissivity up to greater than 0.9 at a wavelength of 6-14 μm, and the emissivity can further be greater than 0.95 at a wavelength of 7-14 μm. As illustrated in FIG. 1, the average emissivity can be almost high up to 0.98. The cells that can be induced in the present invention may comprise fibroblasts, endothelial cells, macrophages, nerve cells, or the like. The composition may be in a lump, granular, powdered or thin-film form. Additionally, the composition used for increasing calmodulin according to the present invention may comprise a matrix or filler. The matrix or filler may comprise materials such as metal, glass, ceramics or polymers. The present invention can be fully applied to a living environment by mixing the far-infrared releasing substance into the matrix or filler. For example, if the far-infrared releasing substance is blended into the window glass of a building, the subject who lives in the building will receive far-infrared rays released by the far-infrared releasing substance, so as to achieve the purpose of increasing calmodulin.

EXAMPLE II

Method for Increasing Calmodulin

Figure 2:
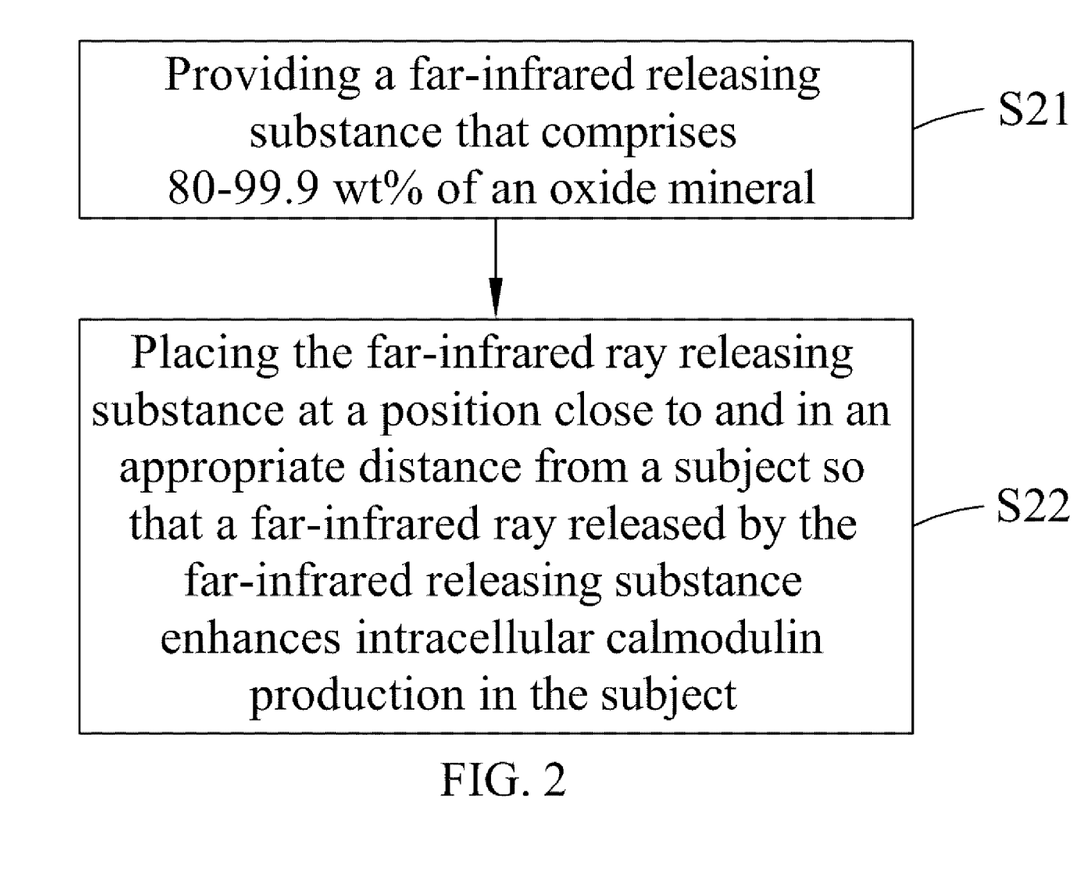
FIG. 2 is a flow chart of a method for increasing calmodulin according to the present invention.

Referring to FIG. 2, a flow chart of a method for increasing calmodulin according to the present invention is illustrated. In this figure, the method for increasing calmodulin comprising: step S21, providing a far-infrared releasing substance that comprises 80-99.9 wt % of an oxide mineral; and step S22, placing the far-infrared ray releasing substance at a position close to and in an appropriate distance from a subject so that a far-infrared ray released by the far-infrared releasing substance enhances intracellular calmodulin production in the subject. The far-infrared releasing substance may be a ceramic mineral and comprises 0.1-20 wt % of a non-oxide mineral such as titanium boride, zinc hydroxide or carbide, in addition to 80-99.9 wt % of an oxide mineral. The oxide mineral may comprise 60-95 wt % of mineral alumina, and may further comprise titanium dioxide, titanium boride, magnesium oxide, silicon oxide, ferric oxide or zinc oxide. Besides, the appropriate distance at which the far-infrared releasing substance is placed from the subject is within an irradiation range of the far-infrared ray. Other properties of the far-infrared releasing substance are the same as those in Example I and will be explained in no more detail.

EXAMPLE III

Effect of Far-Infrared Releasing Substance on Increasing Calmodulin in RAW Cells RAW 264.7 Cell Culture RAW 264.7 monocyte/marcrophage cell lines were cultured in DMEM media, and the cell concentration was adjusted to $1\times10^6$ cells/ml in each 10-cm culture dish. 100 grams of the far-infrared releasing substance according to the present invention were packed in a packaging bag. The material of the packaging bag may include synthetic or natural polymers, metals, glass or ceramics, etc. The group that the packaging bag was uniformly placed under the culture dish in which RAW 264.7 cells were cultured, namely, the composition of the present invention does not directly contact with the cells, used as an experiment group (FIR group). The group that the composition of the present invention is not placed under the cells was used as an control group. Next, the FIR group and the control group were respectively incubated in different incubators under 5% $CO_2$ at 37° C., and taken out respectively after incubation for 1, 2, 3 and 4 days. The calmodulin contents in the cells in the culture dishes were analyzed using Western blotting. Moreover, In another experiment, 600 ng/ml of lipopolysaccharide (LPS) was added into the cells to co-incubate.

Detecting Calmodulin Contents by Western blotting

When the time point was reached, the cells were removed from the culture dishes and washed with a PBS buffer twice. The PBS buffer was removed, followed by addition of a lysis buffer. The mixed solution was stored at −20° C. overnight, and was centrifuged to obtain the supernatant. The calmodulin content in the supernatant was detected by Western blotting. The results are shown below.

Figure 3A:
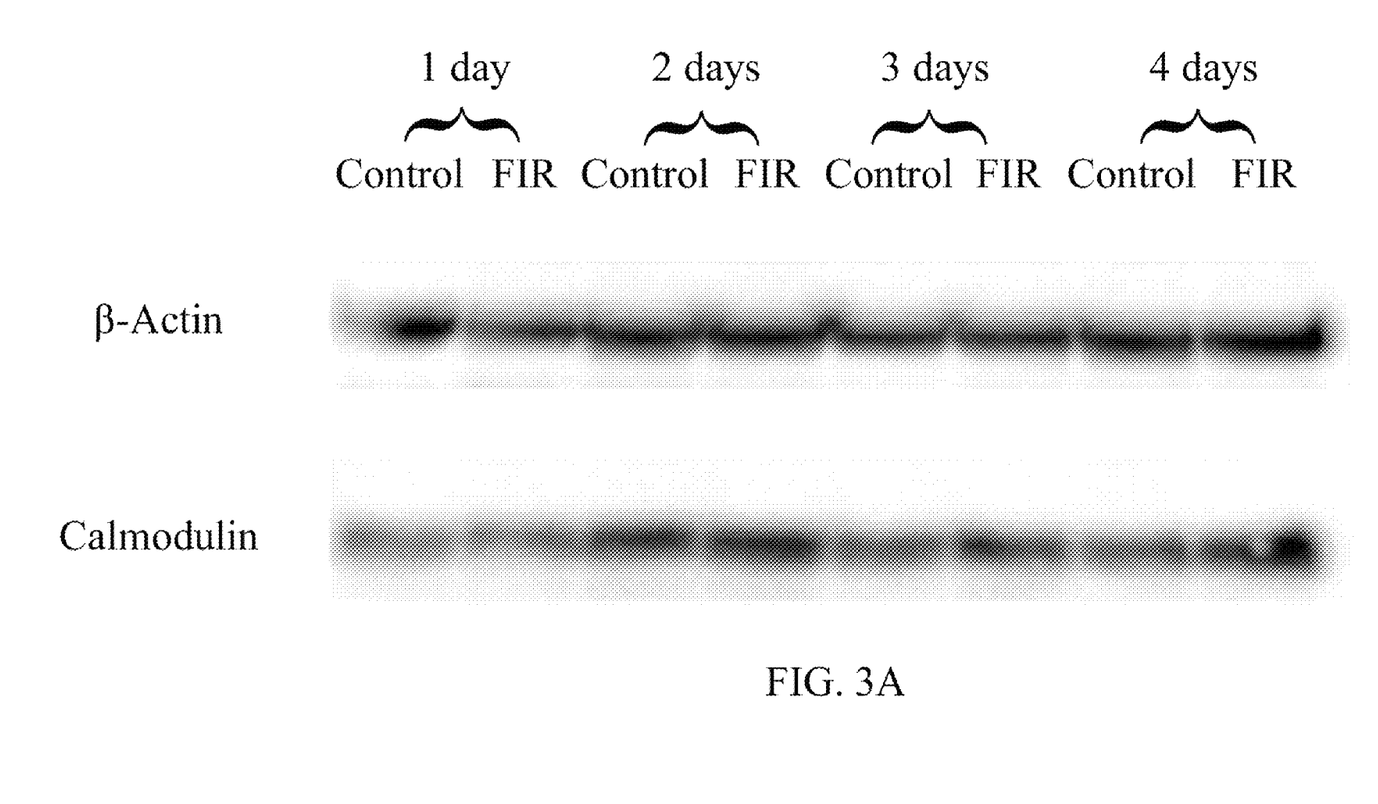
FIG. 3A is a photograph showing the calmodulin contents detected by Western blotting.
Figure 3B:
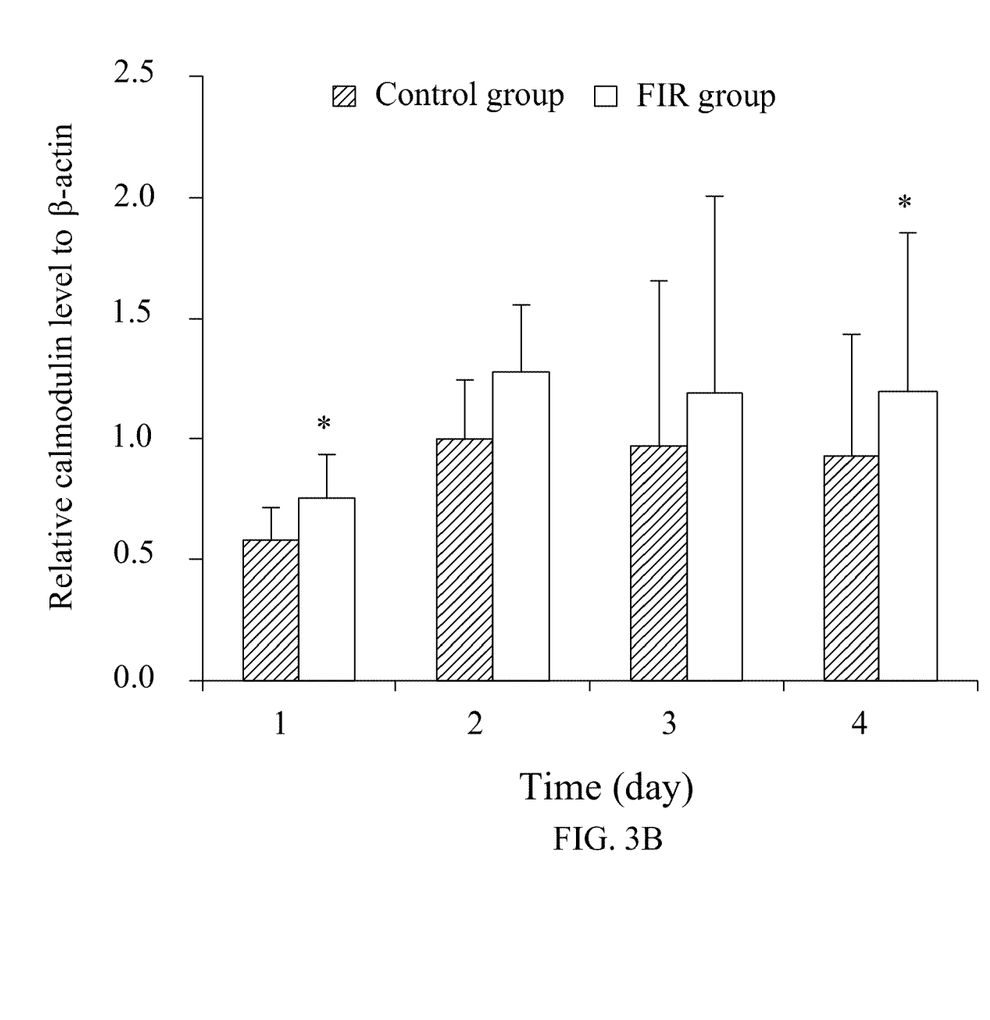
FIG. 3B is a bar chart showing the incubation time vs. the calmodulin contents.

Referring to FIG. 3, it shows the influence of the release time of far-infrared rays on the calmodulin contents in RAW 264.7 cells incubated without addition of LPS according to the present invention, wherein FIG. 3A is a photograph showing the calmodulin contents detected by Western blotting, and FIG. 3B is a bar chart showing the incubation time vs. the calmodulin contents. As can be seen from these figures, the calmodulin contents in the cells incubated using the composition of the present invention (FIR group) are more than the calmodulin contents in the control group at all the time points. It is demonstrated that the far-infrared releasing substance allows increased contents of calmodulin in cells. It is apparent that the far-infrared releasing substance has a good effect of enhancing intracellular production of calmodulin.

Figure 4A:
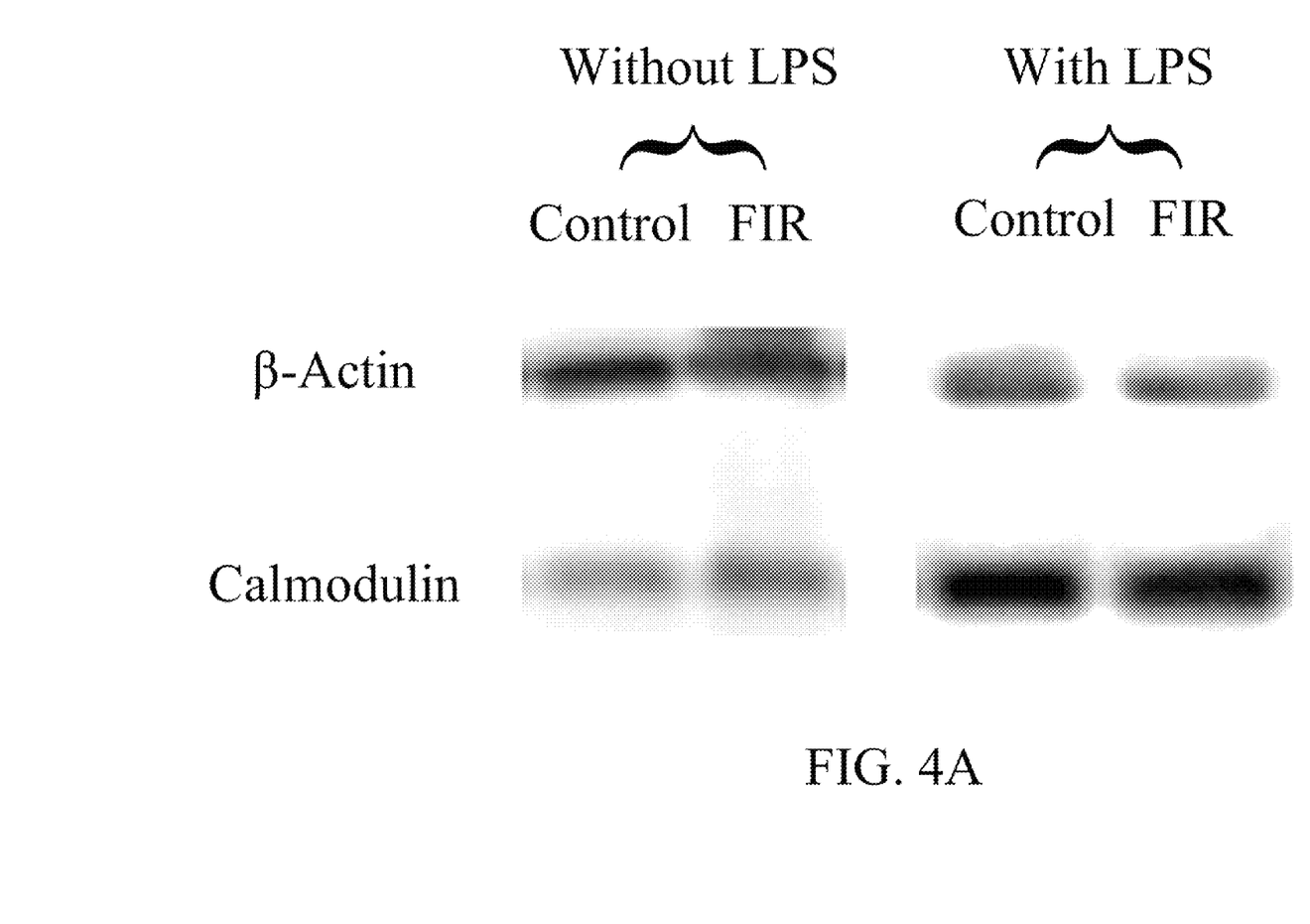
FIG. 4A is a photograph showing the calmodulin contents detected by Western blotting.
Figure 4B:
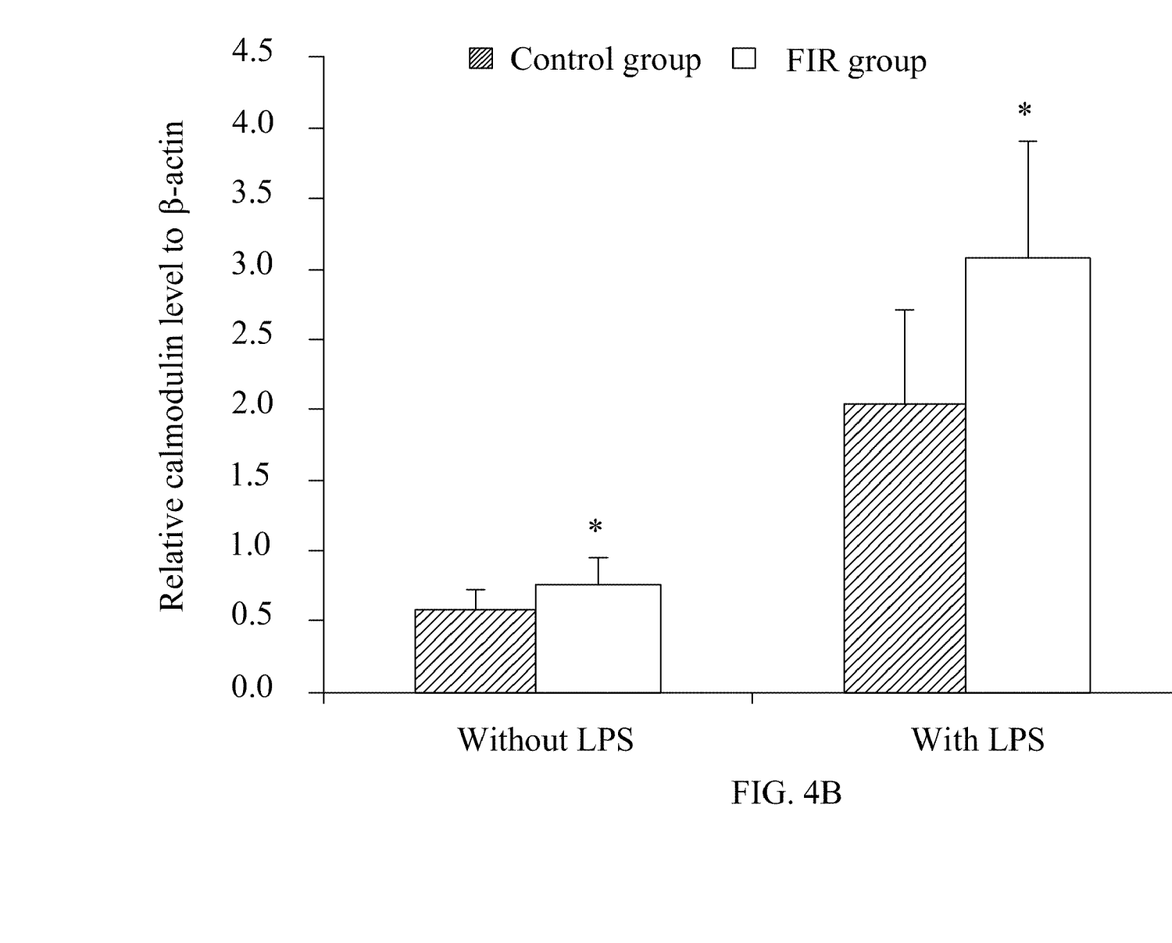
FIG. 4B is a bar chart showing addition or no addition of LPS vs. the calmodulin contents.

Referring to FIG. 4, it shows the influence of addition or no addition of LPS in incubation of RAW 264.7 cells on the calmodulin contents according to the present invention, wherein FIG. 4A is a photograph showing the calmodulin contents detected by Western blotting, and FIG. 4B is a bar chart showing addition or no addition of LPS vs. the calmodulin contents. As can be seen from these figures, no matter the cells are incubated with or without addition of LPS, the FIR group in which the far-infrared releasing substance exists always contains higher calmodulin contents than the control group. It is demonstrated that the presence of such radioactive substance can enhance intracellular production of calmodulin.

EXAMPLE IV

Figure 5:
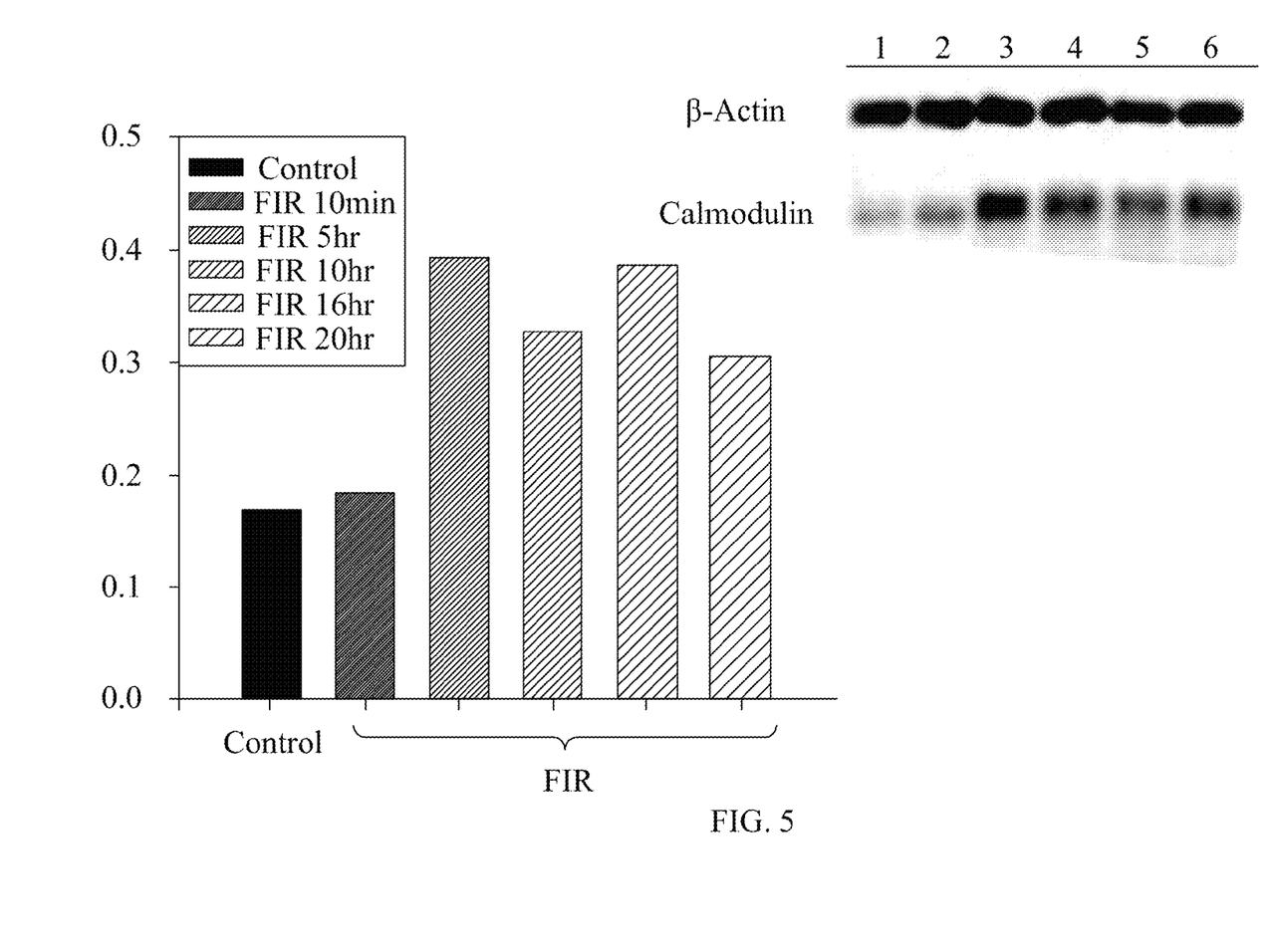
FIG. 5 shows a Western blotting photograph showing the influence of the far-infrared releasing substance according to the present invention on the calmodulin contents in vascular endothelial cells and a bar chart showing the calmodulin contents.

Effect of Far-Infrared Releasing Substance on Increasing Calmodulin in Vascular Endothelial Cells Referring to FIG. 5, it shows a Western blotting photograph showing the influence of the far-infrared releasing substance according to the present invention on the calmodulin contents in vascular endothelial cells and a bar chart showing the calmodulin contents. The cell culture and experimental procedure are similar to Example III and will be explained in no more detail. As can be clearly seen from these figures, no matter how long the far-infrared releasing substance irradiates far-infrared rays, calmodulin production in vascular endothelial cells can be enhanced. It is demonstrated that the far-infrared releasing substance has a good effect of enhancing calmodulin production in vascular endothelial cells.

EXAMPLE V

Figure 6:
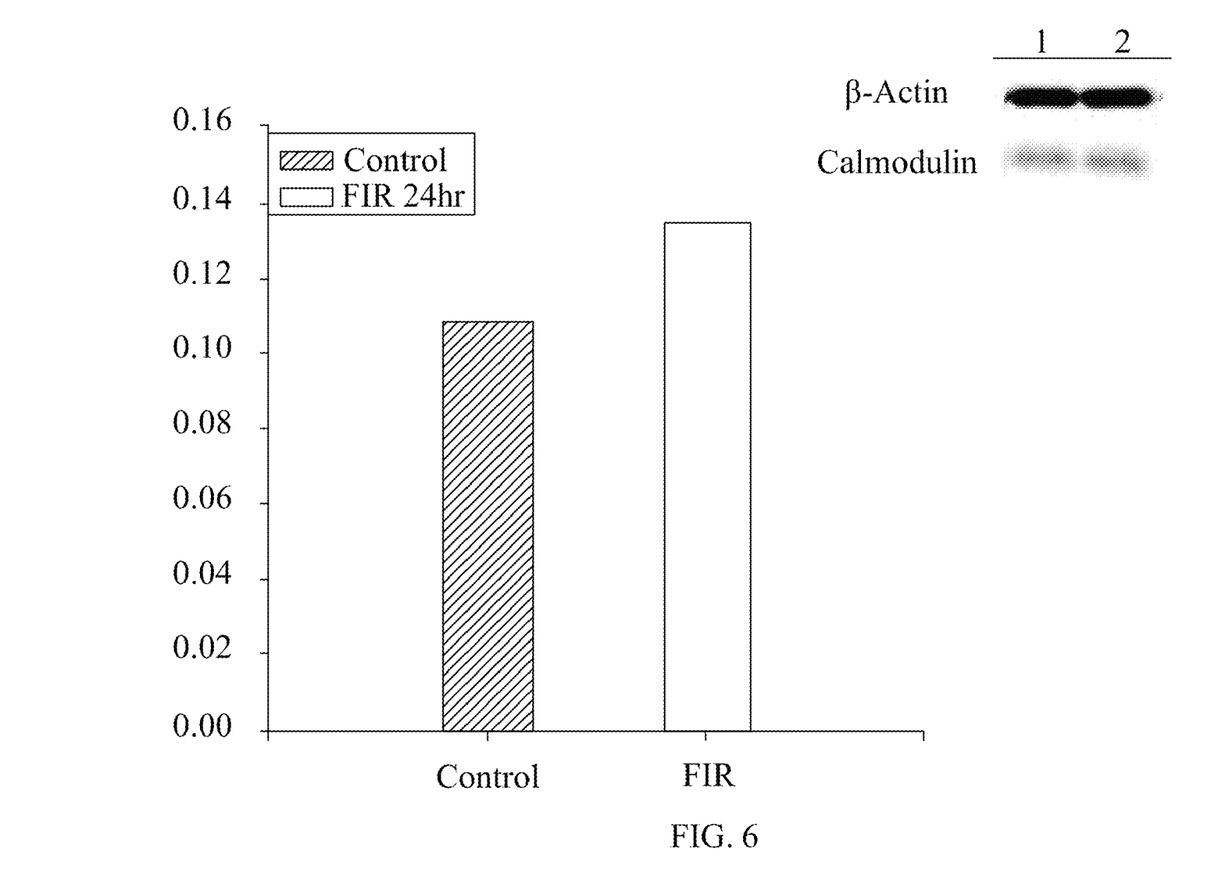
FIG. 6 shows a Western blotting photograph showing the influence of the far-infrared releasing substance according to the present invention on the calmodulin contents in stellate nerve cells and a bar chart showing the calmodulin contents.

Effect of Far-Infrared Releasing Substance on Increasing Calmodulin in Stellate Nerve Cells Referring to FIG. 6, it shows a Western blotting photograph showing the influence of the far-infrared releasing substance according to the present invention on the calmodulin contents in stellate nerve cells and a bar chart showing the calmodulin contents. The cell culture and experimental procedure are similar to Example III and will be explained in no more detail. As can be clearly seen from these figures, far-infrared rays released by the far-infrared releasing substance have the function of enhancing calmodulin production in stellate nerve cells. It is demonstrated that the far-infrared releasing substance has a good effect of enhancing calmodulin production in stellate nerve cells.

The above description is illustrative only and is not to be considered limiting. Various modifications or changes can be made without departing from the spirit and scope of the invention. All such equivalent modifications and changes shall be included within the scope of the appended claims.

What is claimed is:

1. A method of using a far-infrared ray releasing substance to enhance production of calmodulin, comprising:
   placing the far-infrared ray releasing substance in an appropriate distance from a subject so that a far-infrared ray released by the far-infrared releasing substance enhances production of calmodulin in cells of the subject;
   wherein the far-infrared releasing substance is a ceramic mineral and comprises 80-99.9 wt % of an oxide mineral, and the appropriate distance is within an irradiation range of the far-infrared ray.

2. The method as claimed in claim 1, wherein the oxide mineral comprises 60-95 wt % of alumina.

3. The method as claimed in claim 2, wherein the oxide mineral further comprises titanium dioxide, titanium boride, magnesium oxide, silicon oxide, ferric oxide or zinc oxide.

4. The method as claimed in claim 1, wherein the far-infrared releasing substance further comprises titanium boride, zinc hydroxide or carbide.

5. The method as claimed in claim 4, wherein the carbide comprises calcium carbide.

6. The method as claimed in claim 1, wherein the far-infrared releasing substance irradiates the far-infrared ray at room temperature.

7. The method as claimed in claim 6, wherein the far-infrared emissivity is greater than 0.9 at a wavelength of 6-14 μm.

8. The method as claimed in claim 7, wherein the far-infrared emissivity is further greater than 0.95 at a wavelength of 7-14 μm.

9. The method as claimed in claim 1, wherein the cells comprise fibroblasts, endothelial cells, macrophages or nerve cells.

* * * * *